(12) United States Patent
Hanash et al.

(10) Patent No.: US 6,680,172 B1
(45) Date of Patent: Jan. 20, 2004

(54) TREATMENTS AND MARKERS FOR CANCERS OF THE CENTRAL NERVOUS SYSTEM

(75) Inventors: Samir M. Hanash, Ann Arbor, MI (US); David Rickman, Ann Arbor, MI (US); Rachana Tyagi, Philadelphia, PA (US); Xiao-Xiang Zhu, Ann Arbor, MI (US); Phillip Kish, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/571,479

(22) Filed: May 16, 2000

(51) Int. Cl.[7] .......................... C12Q 1/60; C07H 21/02; C07H 21/04; G01N 33/53
(52) U.S. Cl. .......................... 435/7.1; 435/6; 536/23.1
(58) Field of Search .................... 435/7.1, 6; 536/23.1

(56) References Cited

U.S. PATENT DOCUMENTS

| | | |
|---|---|---|
| 3,687,808 A | 8/1972 | Merigan, Jr. et al. |
| 4,426,330 A | 1/1984 | Sears |
| 4,469,863 A | 9/1984 | Ts'o et al. |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,683,195 A | 7/1987 | Mullis et al. |
| 4,683,202 A | 7/1987 | Mullis |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,965,188 A | 10/1990 | Mullis et al. |
| 4,981,957 A | 1/1991 | Lebleu et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |

(List continued on next page.)

FOREIGN PATENT DOCUMENTS

| | | |
|---|---|---|
| WO | WO 93/24510 | 12/1993 |
| WO | WO 94/26764 | 11/1994 |
| WO | WO 97/30731 | 8/1997 |

(List continued on next page.)

OTHER PUBLICATIONS

Szymocha, et al. Human T–cell Lymphotropic Virus Type 1 Infected T Lymphocytes Impair Catabolism and Uptake of Glutamate by Astrocytes via Tax–1 and Tumor Necrosis Factor Alpha. Journal of Virology. Jul. 2000, Vol 74, No. 14 p 6433–6441.*

Wolfer et al. Expression of the axon growth–related neural adhesion molecule TAG–1/axonin–1 in the adult mouse brain. Anat. Embryol. 1998, 197:177–185.*

(List continued on next page.)

*Primary Examiner*—Karen Lacourciere
(74) *Attorney, Agent, or Firm*—Medlen & Carroll, LLP

(57) ABSTRACT

The present invention relates to novel cancer markers and compositions and methods for cancer therapies. For example, the present invention provides compositions and methods for the detection of gene expression of particular marker genes as indicative of cancers, while control of said gene expression provides for intervention in cancer therapies and, in particular, glioma therapies.

9 Claims, 6 Drawing Sheets

U.S. PATENT DOCUMENTS

| | | |
|---|---|---|
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,016 A | 5/1995 | Low et al. |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,127 A | 10/1995 | Felgner et al. |
| 5,459,255 A | 10/1995 | Cook et al. |
| 5,462,854 A | 10/1995 | Coassin et al. |
| 5,446,677 A | 11/1995 | Baxter et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,534,259 A | 7/1996 | Zalipsky et al. |
| 5,536,633 A | 7/1996 | Lok |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,350 A | 9/1996 | Madsack |
| 5,556,948 A | 9/1996 | Tagawa et al. |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,583,020 A | 12/1996 | Sullivan |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |

| | | |
|---|---|---|
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,705,188 A | 1/1998 | Junichi et al. |
| 5,714,331 A | 2/1998 | Buchardt et al. |
| 5,719,262 A | 2/1998 | Buchardt et al. |
| 5,750,692 A | 5/1998 | Cook et al. |
| 5,824,544 A | 10/1998 | Arlmentano et al. |
| 5,830,730 A | 11/1998 | German et al. |
| 5,872,154 A | 2/1999 | Wilson et al. |
| 5,885,808 A | 3/1999 | Spooner et al. |
| 5,981,225 A | 11/1999 | Kuchanek et al. |
| 5,994,069 A | 11/1999 | Hall et al. |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,529 A | 11/1999 | Feuerstein et al. |
| 6,001,557 A | 12/1999 | Wilson et al. |
| 6,019,978 A | 2/2000 | Ertl et al. |
| 6,033,908 A | 3/2000 | Bout et al. |
| 6,287,835 B1 * | 9/2001 | Croteau et al. |

FOREIGN PATENT DOCUMENTS

| | | |
|---|---|---|
| WO | WO 98/34485 | 8/1998 |
| WO | WO 99/02685 | 1/1999 |
| WO | WO 00/09675 | 2/2000 |
| WO | WO 00/12738 | 3/2000 |

OTHER PUBLICATIONS

Kozlov et al., The Human TAX1 Gene Encoding the Axon–Associated cell Adhesion Molecule TAG–1/Axonin–1: Genomic Structure and Basic Promoter. Genomics (30) 1995, p 141–148.*
Maniatis et al., Science 236:1237 [1987].
Voss et al., Trends Biochem. Sci., 11:287 [1986].
Anderson and Young, Quantitative Filter Hybridization, in *Nucleic Acid Hybridization* [1985].
Dijkema et al., EMBO J. 4:761 [1985].
Uetsuki et al., J. Biol. Chem., 264:5791 [1989].
Kim et al., Gene 91:217 [1990].
Sambrook et al., *Molecular Cloning: A Laboratory Manual*, 2nd ed., Cold Spring Harbor Laboratory Press, New York [1989], pp. 16.7–16.8.
Mizushima and Nagata, Nuc. Acids. Res., 18:5322 [1990].
Gorman et al., Proc. Natl. Acad. Sci. USA 79:6777 [1982].
Boshart et al., Cell 41:521 [1985].
Kacian et al., Proc. Natl. Acad. Sci. USA 69:3038 [1972].
Chamberlin et al., Nature 228:227 [1970].
Wu and Wallace, Genomics 4:560 [1989].
H.A. Erlich (ed.), *PCR Technology*, Stockton Press [1989].
Graham and van der Eb, Virol., 52:456 [1973].
Hasler et al., Eur. J. Biochem., 211:329 [1993].
Karagogeos et al., J. Comp. Neurol., 379:415 [1997].
Hatada et al., Proc. Natl. Acad. Sci. USA 88:9523 [1991].
Asakawa et al., Proc. Natl. Acad. Sci. USA 91:9052 [1994].
Larsen et al., Genomics 13:1095 [1992].
Wimmer et al., Genomics 38:124 [1996].
Kenwrick et al., Hum. Molec. Genet., 2:1461 [1993].
Merzak et al., Molecular Brain Research 41:1–7 (1996).
Kozlov et al., Genomics 30:141 [1995].
Ausbel et al., eds. *Current Protocols in Molecular Biology*, New York, John Wiley & Sons, Inc., [1994].
Karagogeos et al., J. Comp. Neurol., 379:415 [1997].
Wolfer et al., J. Comp. Neurol., 345:1 [1994].
Kleihues et al., Brain Pathol., 3:255 [1993].
Bignami et al., Brain Res., 43:429 [1972].
Furley et al., Cell 61:157 [1990].
Kunz et al., J. Cell Biol., 143:1673 [1998].
Felsenfeld et al., Neuron 12:675 [1994].
Bjerkvig et al., J. Neurosurg., 72:463 [1990].
Pilkington, Brain Pathol., 4:157 [1994].
Pignatelli and Vessey, Hum. Pathol., 25:849 [1994].
Nielsen et al., Science 254:1497 [1991].
Martin et al., Helv. Chim. Acta 78:486 [1995].
Koehler and Milstein (Nature 256:495 [1975].
Tsiortra et al., J. Biol. Chem., 271:29216 [1996].
Izumoto et al., Cancer Research 56:1440 [1996].
Chen et al., "Gene therapy for brian tumors: regression of experimental gliomas by adenovirus–mediated gene transfer in vivo," PNAS 91:3054 [1994].
Asakawa et al., "Genetic variation detected by quantitative analysis of end–labeled genomic DNA fragments," PNAS 91:9052 [1994].
Rickman et al., "Distinctive molecular profiles of high–grade and low–grade gliomas blased on olignoucleotide microarray analysis," *Cancer Research* 61:6885 2001.
Rickman et al., "The gene for the anoxal cell adhesion molecule TAX–1 is amplified and aberrantly expressed in malignant gliomas," *Cancer Research* 61:2162 [2001].

* cited by examiner

FIGURE 6 (SEQ ID NO:5)

```
AGCGGCCCAGACAGGGGCTGGCGGCCCGGCCGGCCCCGGCTCACCGACTCGGGCAGCATCCACCTGCCCC
AGCCAACACCCTTCTCTCGCCCCAGGTCCTTTCTCAGCCTCCAGCTGGGCTGTCCCCAAGCTGAGCTGAG
GCTCTTCTCCTCCGATCCCCACCTCTGCCCGGACATCCACCATGGGACAGCCACCAGGAGGAAGCCACA
CCTGCTGCTGGTAGCTGCTGTGGCCCTTGTCTCCTCTTCAGCTTGGAGTTCAGCCCTGGGATCCCAAACC
ACCTTCGGGCCTGTCTTTGAAGACCAGCCCCTCAGTGTGCTATTCCCAGAGGAGTCCACGGAGGAGCAGG
TGTTGCTGGCATGCCGCGCCCGGGCCAGCCCTCCAGCCACCTATCGGTGGAAGATGAATGGTACCGAGAT
GAAGCTGGAGCCAGGTTCCCGTCACCAGCTGGTGGGGGGCAACCTGGTCATCATGAACCCCACCAAGGCA
CAGGATGCCGGGGTCTACCAGTGCCTGGCCTCCAACCCAGTGGGCACCGTTGTCAGCAGGGAGGCCATCC
TCCGCTTCGGCTTTCTGCAGGAATTCTCCAAGGAGGAGCGAGACCCAGTGAAAGCTCATGAAGGCTGGGG
GGTGATGTTGCCCTGTAACCCACCTGCCCACTACCCAGGCTTGTCCTACCGCTGGCTCCTCAACGAGTTC
CCCAACTTCATCCCGACGGACGGGCGTCACTTCGTGTCCCAGACCACAGGGAACCTGTACATTGCCCGAA
CCAATGCCTCAGACCTGGGCAACTACTCCTGTTTGGCCACCAGCCACATGGACTTCTCCACCAAGAGCGT
CTTCAGCAAGTTTGCTCAGCTCAACCTGGCTGCTGAAGATACCCGGCTCTTTGCACCCAGCATCAAGGCC
CGGTTCCCAGCAGAGACCTATGCACTGGTGGGGCAGCAGGTCACCCTGGAGTGCTTCGCCTTTGGGAACC
CTGTCCCCCGGATCAAGTGGCGCAAAGTGGACGGCTCCCTGTCCCCGCAGTGGACCACAGCTGAGCCCAC
CCTGCAGATCCCCAGCGTCAGCTTTGAGGATGAGGGCACCTACGAGTGTGAGGCGGAGAACTCCAAGGGC
CGAGACACCGTGCAGGGCCGCACATCATCGTGCAGGCTCAGCCTGAGTGGCTAAAAGTGATCTCGGACACAG
AGGCTGACATTGGCTCCAACCTGCGTTGGGGCTGTGCAGCCGCCGGCAAGCCCCGGCCTACAGTGCGCTG
GCTGCGGAACGGGGAGCCTCTGGCCTCCCAGAACCGGGTGGAGGTGTTGGCTGGGGACCTGCGGTTCTCC
AAGCTGAGCCTGGAAGACTCGGGCATGTACCAGTGTGTGGCAGAGAATAAGCACGGTACCATCTACGCCA
GCGCCGAGCTAGCCGTGCAAGCACTCGCCCCTGACTTCAGGCTGAATCCCGTGAGGCGTCTGATCCCCGC
GGCCCGCGGGGAGAGATCCTTATCCCCTGCCAGCCCCGGGCAGCTCCAAAGGCCGTGGTGCTCTGGAGC
AAAGGCACGGAGATTTTGGTCAACAGCAGCAGAGTGACTGTAACTCCAGATGGCACCTTGATCATAAGAA
ACATCAGCCGGTCAGATGAAGGCAAATACACCTGCTTTGCTGAGAACTTCATGGGCAAAGCCAACAGCAC
TGGAATCCTATCTGTGCGAGATGCAACCAAAATCACTCTAGCCCCCTCAAGTGCCGACATCAACTTGGGT
GACAACCTGACCCTACAGTGCCATGCCTCCCACGACCCCACCATGGACCTCACCTTCACCTGGACCCTGG
ACGACTTCCCCATCGACTTTGATAAGCCTGGAGGGCACTACCGGAGAACTAATGTGAAGGAGACCATTGG
GGATCTGACCATCCTGAACGCCCCAGCTGCGCCATGGGGGGAAGTACACGTGCATGGCCCAGACGGTGGTG
GACAGCGCGTCCAAGGAGGCCACAGTCCTGGTCCGAGGTCCGCCAGGTCCCCCAGGAGGTGTGGTGGTGA
GGGACATTGGCGACACCACCATCCAGCTCAGCTGGAGCCGTGGCTTCGACAACCACAGCCCCATCGCTAA
GTACACCCTGCAAGCTCGCACTCCACCTGCAGGGAAGTGGAAGCAGGTTCGGACCAATCCTGCAAACATC
GAGGGCAATGCCGAGACTGCACAGGTGCTGGGCCTCACCCCCTGGATGGACTATGAGTTCCGGGTCATAG
CCAGCAACATTCTGGGCACTGGGGAGCCTAGTGGGCCCTCCAGCAAAATCCGGACCAGGGAAGCAGCCCC
CTCGGTGGCACCCTCAGGACTCAGCGGAGGAGGTGGAGCCCCGGAGAGCTCATCGTCAACTGGACGCCC
ATGTCACGGGAGTACCAGAACGGAGACGGCTTCGGCTACCTGCTGTCCTTCCGCAGGCAGGGCAGCACTC
ACTGGCAGACCGCCCGGGTGCCTGGCGCCGATGCCCAGTACTTTGTCTACAGCAACGAGAGCGTCCGGCC
CTACACGCCCTTTGAGGTCAAGATCCGCAGCTACAACCGCCGCGGGATGGGCCCGGAGGCCTCACTGCA
CTCGTGTACTCAGCTGAGGAAGAGCCCAGGGTGGCCCCTACCAAGGTGTGGGCCAAAGGGGTCTCATCCT
CAGAGATGAACGTGACCTGGGAACCCGTGCAGCAGGACATGAATGGTATCCTCCTGGGGTATGAGATCCG
CTACTGGAAAGCTGGGGACAAAGAAGCAGCTGCGGACCGAGTGAGGACAGCAGGGCTGGACACCAGTGCC
CGAGTCAGTGGCCTGCATCCCAACACCAAGTACCATGTGACCGTGAGGGCCTACAACCGGGCTGGCACTG
GGCCTGCCAGCCCTTCTGCCAACGCCACGACCATGAAGCCCCCTCCGCGGCGACCTCCTGGCAACATCTC
CTGGACTTTCTCAAGCTCTAGTCTTAGCATTAAGTGGGACCCTGTGGTCCCTTTCCGAAATGAGTCTGCA
GTCACCGGCTATAAGATGCTGTACCAGAATGACTTACACCTGACTCCCACGCTCCACCTCACCGGCAAGA
ACTGGATAGAAATCCCAGTGCCTGAAGACATTGGCCATGCCCTTGGTACAAATTCGGACCACACAGGGCCGG
AGGGGATGGGATCCCTGCAGAAGTCCACATCGTGAGGAATGGAGGCACAAGCATGATGGTGGAGAACATG
GCAGTCCGCCCAGCACCACACCCTGGCACCGTCATTTCCCACTCCGTGGCGATGCTGATCCTCATAGGCT
CCCTGGAGCTCTGATCCTGGAACCCCTCCCTCTGCGCCGCAGCTGGACGCCACCTCCGACGGACACAGCC
AGCCCCTTCCTGCTGCCAAGGTGGCCTGACACTGTGCCAGAGAGTGGCTGGTTTTAAATACCTACTTTAA
ACAGTGCCCTTTTTGTAGGAGGTAGGATATTTTATATTCTGCCGCAGGATAGAACCCACGCAAGGATTTT
CTTTAAATTGAGAGGCACCAGGCAGTAACTTCCATGATGACACTGACGCCTATACCTGAGCTCTAGGCTG
CCTGGAGGGAAGGAACAGGCCCATGGGAAGAAGGGGGTTTTAAAAACATGTCTTCAACTCAGCAGAGATG
GCCCTCTGGGACCCTATACGCACTCCGCCACTTGAGAGCAGTCCTAGGCCCGGCAGGAACACCAGACATG
AACAGGTTGAAGAACTGGAGCGAAGTGCACCTCACCATCCTTCAGTCTAAGGAAGAAGGGCAAGCCCT
GGGACCAAGAGCTCTCCCGCCTTCTCCCTCGAGCAGCAGCAAGGACCCTGACGCTGTCCCCGATAACTCC
CTAGGGGCTCCTGCCTGCCCAAGCGGCTGAGAACCAGCGCCCCGATGCCTGAGGCTGGGAGCCTGAGCCC
CTTCAGCTTTGAGGGGGGTGATACTCCAGGCTGTTTGGGGTGGGAGCCAAAAAGAGTTGAGAGGCCAGGG
CCCTTGGTGGAAAGGGGCACCAGCCTTGGTCTGAGATAGTCACAACCCAGGTGACGATGCCCTCTCAGCC
AACACTGCCAACCTGACCCTGTCATCCCGATTGACAGCGCCACTTCAGGTGGCTGGGTGACTAAAGGGCT
TGTCTTGGTGGGGTCTCCCACCCCTCCAAGACCCATTCTGCACAGTCCCTCCAGGGTTTGGGCAGGAGAT
GGCCAATCATGCGCCCACCTCTCCAGTGCTGCCTGCAGTCAGCTCGGCCTCCCCGACCTGCAGCCCCAGA
CTCTGCTCTCCCAGCACTGACTCACTCCTGCCTGGGAGGGGAATGCAGCATTCATGCTGGTGTGTCCTGG
TATTGGGAGGTTTCTGGGAAGGGCAGAGGATAAATGTGGCCCTGCCTGCTCCCAGGTATACCTAGGACCA
CCTGGCCAGATCCGCTCCCAGACGGCCTTGGACTGCTTGCATTTCCCCGGAGAAAAGGGGTTAATAAAT
GGGCCATCCTTTCCTGAAAAAAAAAAACCCCCCCCCCCAAAAAAAAAAAAAAAAAAAAAAAAAAAAAAA
```

TREATMENTS AND MARKERS FOR CANCERS OF THE CENTRAL NERVOUS SYSTEM

This invention was made with government support under Grant No. CA26803 awarded by the National Institutes of Health. The Government has certain rights in the invention.

FIELD OF THE INVENTION

The present invention relates to novel cancer markers and compositions and methods for cancer therapies. For example, the present invention provides for the detection of gene expression of particular marker genes as indicative of cancers, while control of said gene expression provides for intervention in cancer therapies and, in particular, glioma therapies.

BACKGROUND OF THE INVENTION

The diagnosis of a brain or spinal cord tumor often comes as a shock, leaving confusion, uncertainty, fear, or even anger in its wake. Brain and spinal cord tumors are abnormal growths of tissue found inside the skull or the bony spinal column. The word tumor is used to describe both abnormal growths that are new (neoplasms) and those present at birth (congenital tumors). No matter where they are located in the body, tumors are usually classed as benign (or non-cancerous) if the cells that make up the growth are similar to other normal cells, grow relatively slowly, and are confined to one location. Tumors are called malignant (or cancerous) when the cells are very different from normal cells, grow relatively quickly, and can spread easily to other locations.

In most parts of the body, benign tumors are not particularly harmful. This is not necessarily true in the brain and spinal cord, which are the primary components of the central nervous system (CNS). Because the CNS is housed within rigid, bony quarters (i.e., the skull and spinal column), any abnormal growth can place pressure on sensitive tissues and impair function. Also, any tumor located near vital brain structures or sensitive spinal cord nerves can seriously threaten health. A benign tumor growing next to an important blood vessel in the brain does not have to grow very large before it can block blood flow. Additionally, if a benign tumor is found deep inside the brain, surgery to remove it may be very risky because of the chances of damaging vital brain centers.

When newly formed tumors begin within the brain or spinal cord, they are called primary tumors. Primary CNS tumors rarely grow from neurons (i.e., nerve cells that perform the nervous system's important functions) because once neurons are mature they no longer divide and multiply. Instead, most tumors are caused by out-of-control growth among cells that surround and support neurons. Primary CNS tumors, such as gliomas and meningiomas, are named by the types of cells they contain, their location, or both.

In a small number of individuals, primary tumors may result from specific genetic diseases, such as neurofibromatosis and tuberous sclerosis, or exposure to radiation or cancer-causing chemicals. Although smoking, alcohol consumption, and certain dietary habits are associated with some types of cancers, they have not been linked to primary brain and spinal cord tumors. In fact, the cause of most primary brain and spinal cord tumors remains a mystery. Brain and spinal cord tumors are largely not preventable at this time and many tumors are associated with poor prognoses. For example, for brain stem gliomas the overall median survival time of patients in studies has been 44 to 74 weeks.

Studies suggest that new brain tumors arise in more than 40,000 Americans each year. About half of these tumors are primary, and the remainder are metastatic. Individuals of any age can develop a brain tumor. In fact, they are the second most common cause of cancer-related death in people up to the age of 35, with a slight peak in occurrence among children between the ages of 6 and 9. However, brain tumors are most common among middle-aged and older adults. People in their 60s face the highest risk. Each year 1 of every 5,000 people in this age group develops a brain tumor. Spinal cord tumors are less common than brain tumors with about 10,000 Americans developing primary or metastatic spinal cord tumors each year. Although spinal cord tumors affect people of all ages, they are most common in young and middle-aged adults.

A) Detection

Brain and spinal cord tumors cause many diverse symptoms, which can make detection tricky. Whatever specific symptoms a patient has, the symptoms generally develop slowly and worsen over time. The brain orchestrates behavior, movement, feeling, and sensation. It controls automatic functions like breathing and heartbeat. Many of these important functions are controlled by specialized brain areas. For example, the brain's left and right hemispheres jointly control hearing and vision; the front part of each hemisphere controls voluntary movements, like writing, for the opposite side of the body; and the brain stem is responsible for basic life-sustaining functions, including blood pressure, heartbeat, and breathing. As a result, brain tumors can cause a bewildering array of symptoms depending on their size, type, and location. Certain symptoms are quite specific because they result from damage to particular brain areas. Other, more general symptoms are triggered by increased pressure within the skull as the growing tumor encroaches on the brain's limited space or blocks the flow of cerebrospinal fluid (fluid that bathes the brain and spinal cord). Some of the more common symptoms of a brain tumor include headaches, seizures, nausea, vomiting, vision and hearing problems, behavioral and cognitive symptoms, motor problems, and balance problems. Common symptoms that result from spinal chord tumors include: pain, sensory changes, and motor problems.

Once a physician suspects a brain or spinal cord tumor because of a patient's medical history and symptoms, a variety of further tests are available for diagnosing the tumor. The first test is often a traditional neurological exam. A neurological exam checks eye movement, eye reflexes, and pupil reaction, reflexes, hearing sensation, movement, balance, and coordination. The next step in diagnosing brain tumors often involves X-rays or special imaging techniques and laboratory tests that can detect the presence of a tumor and provide clues about its location and type. Special imaging techniques, especially computed tomography (CT) and magnetic resonance imaging (MRI), have dramatically improved the diagnosis of CNS tumors in recent years. In many cases, these scans can detect the presence of a tumor even if it is less than half-an-inch across. However, the equipment is expensive and complex and such imaging techniques can miss tumors (e.g., small tumors), particularly at early stages where treatment is more likely to succeed. Such equipment also does not provide information relating to the morphological identity of the tumor. A third imaging technique called positron emission tomography (PET) provides a picture of brain activity rather than structure by measuring levels of injected glucose that has been labelled with a radioactive tracer. Glucose is used by the brain for energy. Detectors placed around the head can spot the labelled glucose, and a computer uses the pattern of glucose distribution to form an image of the brain. Since malignant tissue uses more glucose than normal tissue, it shows up on the scan as brighter or lighter than surrounding tissue. Currently, PET is not widely used in tumor diagnosis, in part because the technique requires very elaborate, expensive equipment, including a cyclotron to create the radioactive glucose.

Laboratory tests commonly used include the electroencephalogram (or EEG) and lumbar puncture, also known as the spinal tap. The EEG uses special patches placed on the scalp or fine needles placed in the brain to record electrical currents inside the brain. This recording can help the physician see telltale patterns in the brain's electrical activity that suggest a brain tumor. Repeated EEG recordings can be particularly helpful in determining whether an abnormality in brain activity is getting worse. In lumbar puncture, doctors obtain a small sample of cerebrospinal fluid. This fluid can be examined for abnormal cells or unusual levels of various compounds that suggest a brain or spinal cord tumor. However, these techniques are limited in their ability to decisively identify and characterize tumors. In view of the limitations of current cancer detection technologies, what is needed are tumor-specific markers that can be used to detect early stage cancer (e.g., cancers too small to be detected by conventional techniques) and can provide information about the morphology of the cancer.

B) Treatment

To date, treatment of tumors requires intense therapies with dramatic and sometimes fatal side effects. The three most commonly used treatments are surgery, radiation, and chemotherapy. Surgery to remove as much tumor as possible is usually the first step in treating an accessible tumor—that is, a tumor that can be removed without unacceptable risk of neurological damage. Although research has led to advances in neurosurgery that make it possible for doctors to reach many tumors that were previously considered inaccessible, not all tumor can be treated with surgery. If the tumor is malignant, doctors often recommend additional treatment following surgery, including radiation and/or chemotherapy.

In radiation therapy, the tumor is bombarded with beams of energy that kill tumor cells. Traditional radiation therapy delivers radiation from outside the patient's body, is usually begun a week or two after surgery, and continues for about six weeks. The dosage is fairly uniform throughout the treated areas, making it especially useful for tumors that are large or have infiltrated into surrounding tissue. However, when traditional radiation therapy is given to the brain, it may also cause damage to healthy tissue.

Chemotherapy uses tumor-killing drugs that are given orally or injected into the bloodstream. Because not all tumors are vulnerable to the same anticancer drugs, physicians often use a combination of drugs for chemotherapy. Chemotherapeutic drugs generally kill cells that are actively growing or dividing, making these compounds relatively more effective against malignant tissue, which contains a high proportion of growing and dividing cells, than to most normal cells. Because a high proportion of the cells in the skin, gastrointestinal tract, and other areas are also growing and dividing at any given time, the side effects commonly observed include skin reactions, hair loss, and digestive disturbances. The drugs most commonly used for CNS tumors are known by the initials BCNU (sometimes called carmustine) and CCNU (or lomustine). Each of these techniques poses significant health risks to treated individuals and does not guarantee elimination of the tumor. Surgery and radiotherapy alone are seldom curative; with the best of care, median survival is under one year for many cancers. Moreover, despite major efforts to introduce new adjunctive therapies, the prognosis for patients with malignant gliomas has remained essentially unchanged for the past thirty years. Thus, the art is in need of new therapies that avoid the dangerous and undesired side-effects of current technologies, while allowing effective tumor reduction or elimination.

SUMMARY OF THE INVENTION

The present invention relates to novel cancer markers and compositions and methods for cancer therapies. For example, the present invention provides for the detection of gene expression of particular marker genes as indicative of cancers, while control of said gene expression provides for intervention in cancer therapies and, in particular, glioma therapies.

For example, the present invention provides methods for detecting cancer in a subject suspected of having cancer comprising detecting the presence of TAX-1 in a sample from the subject. In some embodiments of the present invention, the sample comprises cerebrospinal fluid, although any suitable sample may be used. In some embodiments, the subject comprises a human subject. In certain embodiments, the cancer comprises a cancer of the central nervous system. For example, in some embodiments, the cancer of the central nervous system comprises a glioma. In some embodiments of the present invention the detecting of the presence of TAX-1 comprises detecting TAX-1 protein by any suitable means. In some embodiments, TAX-1 protein is detected by exposing TAX-1 protein (e.g., from a cell extract) to a TAX-1-specific antibody and detecting the presence of the antibody (e.g., detecting the presence of an antibody/TAX-1 complex). In other embodiments of the present invention the detection of the presence of TAX-I comprises detecting TAX-1 mRNA by any suitable means. In some embodiments, detecting TAX-1 mRNA comprises exposing TAX-1 mRNA to a nucleic acid probe complementary to TAX-1 mRNA. In some embodiments of the present invention, the detection of the presence of TAX-1 comprises measuring the amount of TAX-1 protein or mRNA in the sample. In certain embodiments, the amount of TAX-1 protein or mRNA is compared to the amount of TAX-1 protein or mRNA from a control sample (e.g., a sample of a subject without cancer and/or a sample of a subject known to have cancer).

The present invention also provides a methods for regulating cell migration by reducing TAX-1 expression, comprising providing: a cell expressing TAX-1 and an agent capable of reducing TAX-1 expression; and exposing the cell to the agent under conditions wherein the agent reduces TAX-1 expression. Any agent that reduces TAX-1 expression finds use with the present invention. In some embodiments, the agent comprises an antisense compound. In certain embodiments, the antisense compound comprises an antisense oligonucleotide. In specific preferred embodiments, the antisense compound comprises SEQ ID NO:1. In other embodiments of the present invention, the agent comprises an antibody. In preferred embodiments, the antibody comprises at least one monoclonal antibody. In some embodiments of the present invention, the exposing of the cell to the agent comprises administering the agent to a subject comprising the cell (e.g., a host, wherein the cell is part of a tissue of the host).

The present invention further provides methods for regulating TAX-1 expression in a subject suspected of having cancer, comprising providing: a subject suspected of having cancer and an agent capable of reducing TAX-1 expression; and administering the agent to the subject under conditions wherein the agent reduces TAX-1 expression. In some embodiments, the method further comprising the step of detecting the expression of TAX-1 in a sample (e.g., a tissue or fluid sample) from the subject. Detection may be made for any number of reasons including, but not limited to, testing the ability of the agent to alter TAX-1 expression. In some embodiments, the agent comprises an antisense compound (e.g., an antisense oligonucleotide including, but not limited to, SEQ ID NO:1). In other embodiments, the agent is an antibody (e.g., one or more polyclonal or monoclonal antibodies).

The present invention also provides methods for testing the ability of a compound to alter TAX-1 expression comprising providing: a cell capable of expressing TAX-1, and a test compound; exposing the cell to the test compound; and detecting the ability of the compound to alter the expression of TAX-1 in the cell. In some embodiments of the present invention, the cell is treated in vitro. In other embodiments, the cell is treated in vivo. In some embodiments, the test compound comprises an antisense compound. In other embodiments, the test compound comprises at least one drug. In preferred embodiment, exposing the test compound to the cell comprises administering the agent to a subject comprising the cell (e.g., a host, wherein the cell is part of a tissue of the host). In other preferred embodiments, the detection of the ability of the test compound to alter expression of TAX-1 comprises detecting a change in cell migration (e.g., using a cell migration assay). In other preferred embodiments, the detection of the ability of the test compound to alter expression of TAX-1 comprises detecting TAX-1 expression.

DESCRIPTION OF THE FIGURES

FIG. 5A shows three representative spheroids that were untreated or treated with the indicated antibody. FIGS. 5B and 5C show graphs indicating migration distances for the spheroids of 5A. FIG. 5D shows RT/PCR products of TAX-1 and GAPDH RNA from the treated cells.

FIG. 6 shows the sequence of *H. sapiens* mRNA for transient axonal glycoprotein (tag-1) (Genbank accession # X68274).

DEFINITIONS

Figure 1:
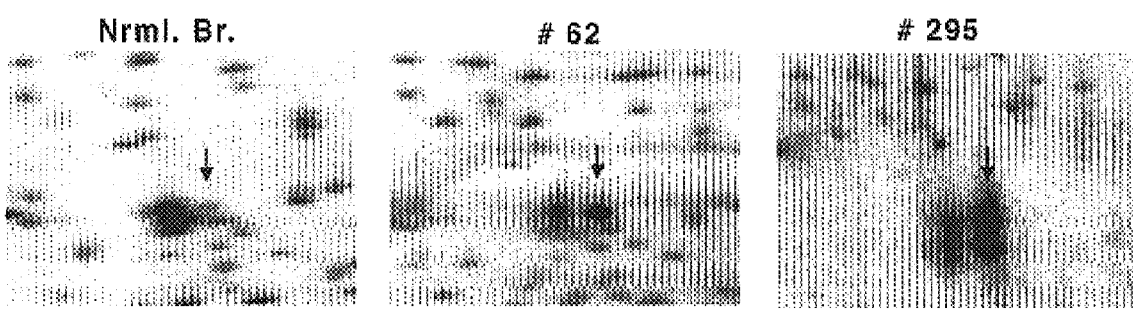
FIG. 1 shows an agarose slab gel analysis of genomic DNA from tumor cells following restriction landmark genome scanning in one embodiment of the present invention.

To facilitate an understanding of the present invention, a number of terms and phrases are defined below:

As used herein, the term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual.

As used herein, the term "host" refers to any animal (e.g., warm blooded mammal), including, but not limited to, humans, non-human primates, rodents, and the like, which is to be the recipient of a particular treatment. Typically, the terms "host" and "patient" are used interchangeably herein in reference to a human subject.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

As used herein, the term "carrier" refers to a diluent, adjuvant, excipient, or vehicle with which a compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

As used herein, the term "therapeutically effective amount" refers to an amount sufficient to reduce by a least about 15 percent, preferably by at least 50 percent, more preferably by at least 90 percent, and most preferably prevent, a clinically significant deficit in the activity, function, and/or response of a host. Alternatively, a therapeutically effective amount is sufficient to cause an improvement in a clinically significant condition in a host.

As used herein, the term "gene targeting" refers to the alteration of genes through molecular biology techniques. Such gene targeting includes, but is not limited to, generation of mutant genes and knockout genes through recombination. When a gene is altered such that its product is no longer biologically active in a wild-type fashion, the mutation is referred to as a "loss-of-function" mutation. When a gene is altered such that a portion or the entirety of the gene is deleted or replaced, the mutation is referred to as a "knockout" mutation.

As used herein, the term "gene transfer system" refers to any means of delivering a composition comprising a nucleic acid sequence to a cell or tissue. For example, gene transfer systems include, but are not limited to vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses and modified viruses) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules that bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows tumor growth).

The term "modulate," as used herein, refers to a change in the biological activity of a biologically active molecule. Modulation encompasses increases and decreases in activity, a change in binding characteristics, or any other change in the biological, functional, or immunological properties of biologically active molecules.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor (e.g., TAX-1). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene encoding a factors that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed). Heterologous genes may be introduced into hematopoietic stem cells through molecular biology manipulation. The coding sequence of the heterologous gene is operatively linked to an expression control sequence. Generally a heterologous gene is first placed into a vector.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with -the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]). Some promoter elements serve to direct gene expression in a tissue-specific manner. For example, the murine α-myosin-heavy chain promoter, α-5.5, promotes expression in a cardiac-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally. at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non- immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk- cell lines, the CAD gene which is used in conjunction with CAD-deficient cells and the mammalian hypoxanthine-guanine phosphoribosyl transferase (hprt) gene which is used in conjunction with hprt - cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "cancers of the nervous tissues" refer to any cancers associated with the central nervous system (e.g., the brain and spinal chord). Such cancer include both primary and secondary tumors. Brain tumors include, but are not limited to astrocytoma, craniopharyngioma, glioma, ependymoma, neuroglioma, oligodendroglioma, glioblastoma multiforme, meningioma, and medulloblastoma. Secondary brain tumors occur from the spread of cancer into the brain from a distant cancerous organ (metastasis). "Gliomas" are a diverse group of brain tumors that arise from the normal "glial" cells of the brain. These cells outnumber the "neurons" that conduct impulses and serve to provide metabolic support to the neurons. The most important determinant of survival for gliomas is the "grade" of the glioma. The low-grade gliomas have a protracted natural history, while the high grade gliomas (anaplastic astrocytoma and glioblastoma multiforme) are much more difficult to successfully treat. The gliomas are associated with specific signs and symptoms that are primarily related to the location of the glioma. Temporal lobe gliomas, for example may cause epilepsy, difficulty with speech or loss of memory. The frontal lobe gliomas may cause behavioral changes, weakness in the extremities (e.g., arms and/or legs) and/or speech difficulty. Occipital gliomas may cause loss of vision and parietal gliomas may cause loss of spatial orientation, diminished sensation on the opposite side of the body, and/or inability to recognize once familiar objects or persons.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

GENERAL DESCRIPTION OF THE INVENTION

The present invention relates to novel cancer markers and compositions and methods for cancer therapies. For example, the present invention provides for the detection of gene expression of particular marker genes as indicative of cancers, while control of said gene expression provides for intervention in cancer therapies and, in particular, glioma therapies.

In one embodiment of the present invention, expression of TAX-1 and related factors are used as cancer markers and/or targets in cancer therapies. The human TAG-1/axonin-1 gene (i.e., TAX-1) encodes a 135 kDa glycoprotein that is transiently expressed on the surface of a subset of neurons during development and is involved in neurite outgrowth (Hasler et al., Eur. J. Biochem., 211:329 [1993] and Karagogeos et al., J. Comp. Neurol., 379:415 [1997]). Using restriction landmark genome scanning during the development of the present invention, TAX-1 was found to be amplified in two high grade gliomas among a group of twenty-six gliomas of different grades. Immunohistochemical analysis demonstrated that the TAX-1 protein was widely expressed in neoplastic glial cells with TAX-1 gene amplification, as well as in glial cells of additional high grade tumors without TAX-1 gene amplification. Since these tumors are highly invasive and in view of the role of TAX-1 in neurite outgrowth, the role of TAX-1 in glioma cell migration was investigated. Using an in vitro assay, it was found that the migration of glioma tumor cells is profoundly reduced in the presence of either an anti-TAX-1 antibody or a TAX-1 antisense oligonucleotide. These findings demonstrated that TAX-1 plays a role in glial tumorigenesis and provides a target for therapeutic intervention.

Thus, the present invention provides novel cancer markers (i.e., TAX-1 and similar and associated factors); methods for detecting, analyzing, and altering cell migration; compositions and methods for altering TAX-1 expression (e.g., antisense, antibody, and genetic approaches); compositions and methods for treating and/or preventing cancer; and compositions and methods for screening assays (e.g., drug screening assays) to identify factors involved in TAX-1 regulation and action, cell migration, and cancer.

DETAILED DESCRIPTION OF THE INVENTION

The role of TAX-1 in cell migration and cancer was originally identified during the development of the present invention using restriction landmark genome scanning. The technique of restriction landmark genome scanning provides a means to search for genomic alterations in tumors (Hatada et al, Proc. Natl. Acad. Sci. USA 88:9523 [1991] and Asakawa et al., Proc. Natl. Acad. Sci. USA 91:9052 [1994]). By utilizing different combinations of enzymes and/or electrophoresis conditions for the separation of restriction digests in two-dimensions (2-D), the number of individual fragments analyzed can reach several thousand. An example of this technique is provided in Example 5, below. The use of the rare cleaving restriction enzyme NotI to digest genomic DNA allows visualization of DNA fragments that occur preferentially in CpG islands of the genome. Because of the localization of the CpG islands in proximity to transcribed sequences, the 2-D patterns obtained with this enzyme are highly targeted to a functional component of the genome (Larsen et al., Genomics 13:1095 [1992]).

Experiments conducted during the development of the present invention utilized the 2-D approach to identify genes amplified in gliomas. In these experiments, 2-D analysis of 26 gliomas was undertaken using the NotI/EcoRV/HinfI enzyme combination. One fragment with first-dimension NotI-EcoRV size of approximately 2300 base pairs and a second-dimension NotI-HinfI size of approximately 1200 base pairs was found to occur with an increased copy number in two of the tumors as shown in FIG. 1. In this Figure, genomic DNA obtained from tumor #295, #62, and normal adult brain was digested with NotI and EcoRV. The fragments were end-labeled and fractionated in a 0.9% disc-agarose gel. The fragments were digested in situ with HinfI and further fractionated in the second dimension in a 5.25% agarose slab gel. The fragment that corresponds to the TAX-1 gene is indicated by the arrow in FIG. 1. Estimated copy numbers of TAX-1 were 140 and 16 copies of the TAX-1 gene per diploid genome for tumors #295 and 62, respectively.

Figure 2:
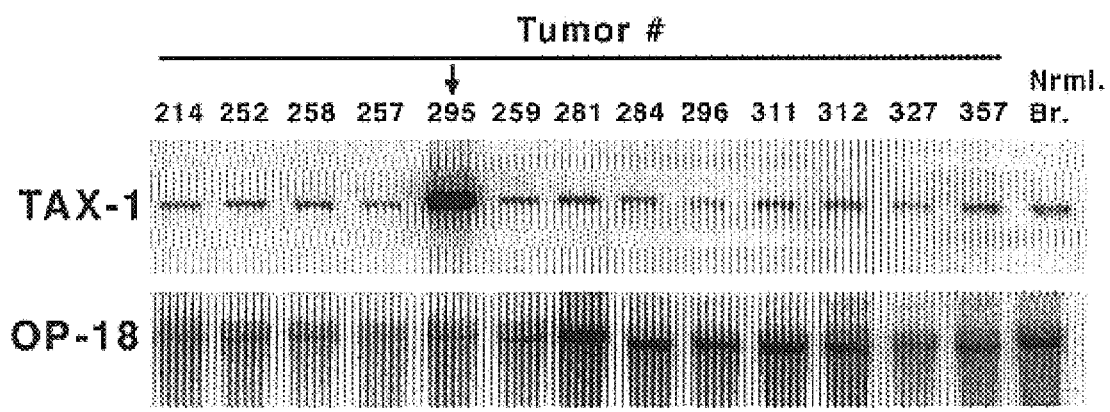
FIG. 2 shows a Southern blot analysis of tumors showing TAX-1 gene amplification in the tumor in one embodiment of the present invention.

The TAX-1 fragment was found to be derived from chromosome 1, based on its occurrence in 2-D patterns of flow sorted chromosome 1 (Wimmer et al., Genomics 38:124 [1996]). This fragment was cloned and sequenced. A database search revealed identity with a sequence in the promoter region of the TAX-1 gene, the human homologue for the "Transiently expressed Axonal Glycoprotein" (TAG-1) found in rats, from position −342 to +32 (Genbank accession number X84419) (Kozlov et al., Genomics 30:141 [1995]). The TAX-1 gene has been mapped to chromosome band 1q32.1 and implicated in microcephaly and Van der Woude syndrome (Kenwrick et al., Hum. Molec. Genet., 2:1461 [1993]). Sufficient DNA was available for Southern blot analysis of 13 of the 26 tumors, including one tumor (#295) which showed amplification of TAX-1 by 2-D analysis. Results of Southern analyses (Ausbel et al., eds. *Current Protocols in Molecular Biology*, New York, John Wiley & Sons, Inc., [1994]) of 13 tumors are shown in FIG. 2, with TAX-1 gene amplification in tumor #295 indicated (arrow). A 641 bp PCR amplified fragment of the most 3' end exon of the TAX-1 gene was used as a probe. The membrane was then exposed to a phosphorimaging screen (Molecular Dynamics) and analyzed (ImageQuant). The membrane was stripped of bound probe and rehybridized with a radiolabeled 740 bp KpnI-BamHI fragment of the OP-18 cDNA, another gene located on chromosome 1.

TAX-1 gene copy number was estimated at 140 copies per diploid genome in tumor #295, consistent with quantitative analysis of TAX-1 spot intensity in 2-D patterns for this tumor. There was no evidence of genomic alterations by Southern blotting in the other twelve tumors.

Figure 3:
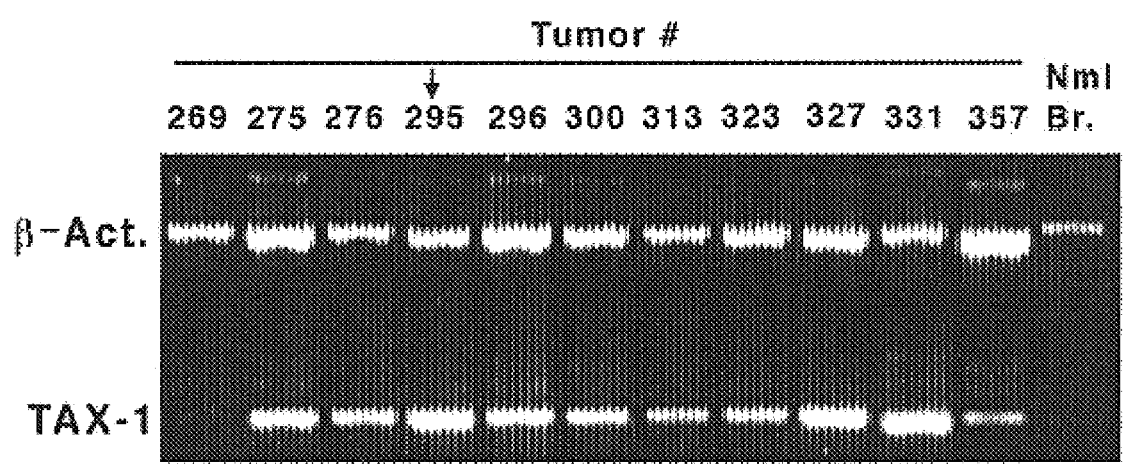
FIG. 3 shows reverse transcriptase/PCR (RT/PCR) results of RNA extracted from tumors and normal human adult brain tissue for TAX-1 and β-actin in one embodiment of the present invention.

Northern analysis of TAX-1 mRNA revealed a low signal in gliomas that could not be reliably quantitated. Therefore, reverse transcription was utilized in combination with polymerase chain reaction (RT/PCR) to evaluate the expression of TAX-1 in gliomas. A PCR product with the expected size (641 bp) was obtained in 18 out of the 19 glioma tumors analyzed. FIG. 3 shows a representative RT/PCR of total RNA extracted from 11 tumors of varying grades (including #295, arrow) and normal human adult brain. The products (641 bp for TAX-1 and 825 bp for β-actin) were fractionated in a 1.5% agarose gel. These results were unexpected, given that in prior studies, TAX-1 was found to be transiently expressed solely on the surface of fasciculating axons of a restricted subset of neurons during embryonic neural development, with minimal expression in normal adult neural tissue (Karagogeos et al., J. Comp. Neurol., 379:415 [1997] and Wolfer et al., J. Comp. Neurol., 345:1 [1994]).

The RT/PCR results suggested that TAX-1 may be expressed in the absence of gene amplification. However, since tumor tissue samples contain a heterogeneous population of cells, the possibility that the PCR product obtained for TAX-1 was derived from non-neoplastic cells within the sample could not be ruled out. Therefore the specificity of expression of TAX-1 by immunohistochemistry was assessed using an antibody against the rat homologue, TAG-1. This antibody recognizes the human TAX-1 protein and has been utilized to monitor TAX-1 expression during human spinal cord development (Karagogeos et al., J. Comp. Neurol., 379:415 [1997]).

Paraffin sections from 29 gliomas, including 12 from the original 26 tumors and which consisted of 21 high grade (Grade III and IV or glioblastoma multiform (GBM), using the World Health Organization criteria) (Kleihues et al., Brain Pathol., 3:255 [1993]), and 8 low grade gliomas (Grade II and pilocytic astrocytomas), were screened for reactivity with the anti-TAX-1 antibody. All but one of the high grade tumors stained positive for TAX-1, while the low grade tumors showed little or no TAX-1 expression (GFAP was used as a control and tested positive in both high and low grade tumors). The brightest and most extensive staining was observed in GBMs, particularly in cells that also expressed GFAP, a marker for cells of glial lineage (Bignami et al., Brain Res., 43:429 [1972]). The subcellular localization of TAX-1 varied between tumors as well as between individual cells within tumors. TAX-1 was found to be associated with the plasma membrane, in the cytoplasm or occasionally forming a perinuclear rim. In contrast, cellular constituents in normal brain, including glial cells showed negative immunostaining for TAX-1.

Figure 4:
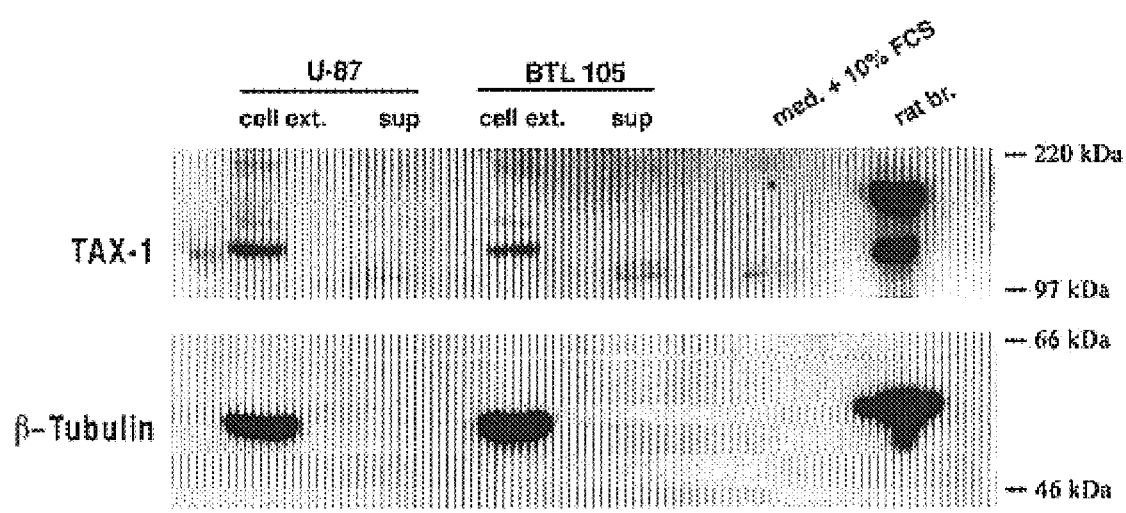
FIG. 4 shows TAX-1 analysis by Western blotting in one embodiment of the present invention.

The TAX-1 protein has been implicated in the promotion of neurite outgrowth of developing neurons via homophilic and heterophilic interactions with L1, integrins and other cell adhesion molecules (Furley et al., Cell 61:157 [1990]; Kunz et al., J. Cell Biol., 143:1673 [1998]; and Felsenfeld et al., Neuron 12:675 [1994]). The TAX-1 protein is attached to the cell membrane by a glycosyl phosphatidylinositol (GPI) anchor which may be cleaved, resulting in the release of a secreted form of TAX-1 from the cell surface (Hasler et al., supra). The secreted form of TAX-1 has been shown to stimulate neurite outgrowth (Hasler et al., supra). Therefore, TAX-1 expression in cultured glioma cells was examined in response to the inhibition of TAX-1. Expression of TAX-1 was observed in both primary glioma cells that were derived from a GBM explant (BTL105 cells) and in cells from an established cell line derived from a Grade III astrocytoma (U87, ATCC #HTB14), based on RT/PCR, immunofluorescence and Western analysis. TAX-1 was detected in the cell lysates of BTL105 and U87 but not in the culture media in which the cells were grown as shown in the Western blot (See, FIG. 4). After 72 hours in culture, the medium/supernatant from both U87, and BTL105 cells was collected separately, concentrated ten fold and subjected to SDS-PAGE/Western blot analysis along with the corresponding cell lysate, concentrated control medium and rat brain extract (indicated as "rat br." in FIG. 4) supplied with the anti-TAX-1 antibody as positive control from Transduction Laboratories. After transferring the proteins to a PVDF membrane, the membrane was probed with a rabbit polyclonal antibody to the TAX-1 protein (Transduction Laboratories). The membrane was stripped and re-probed with an antibody against β-tubulin (Sigma).

Figure 5:
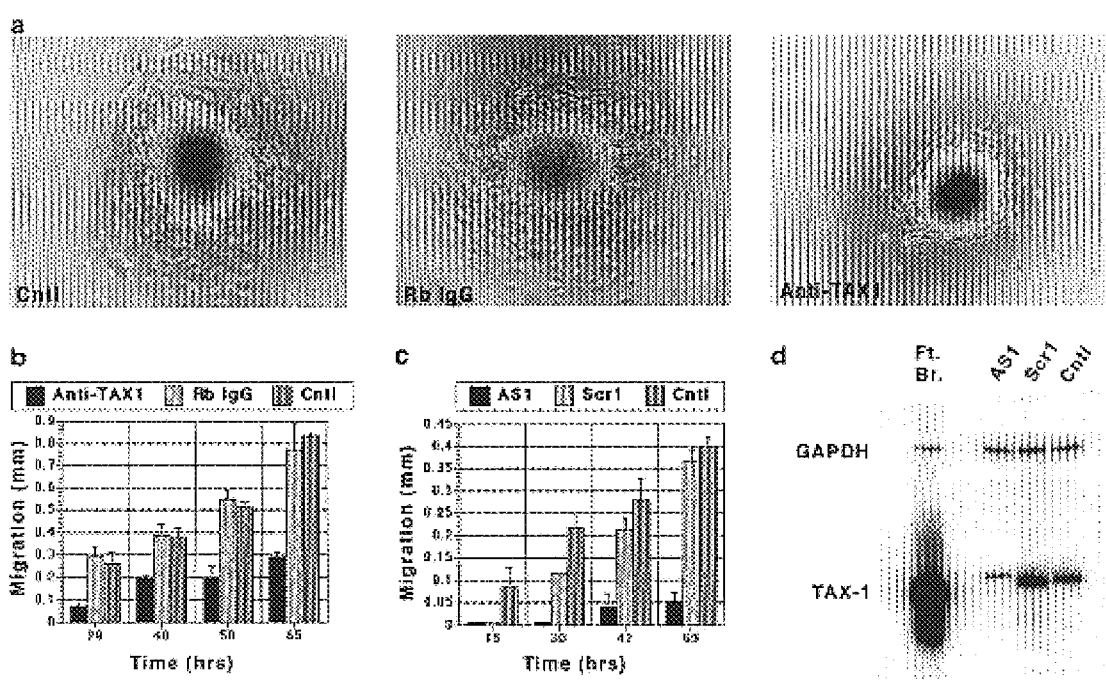
FIGS. 5A–D shows the effect of TAX-1 on the migration of glioma cells.

Since malignant gliomas are highly invasive, an in vitro assay was utilized using U87 and/or BTL105 cells, to assess the involvement of TAX-1 in cell migration (Bjerkvig et al., J. Neurosurg., 72:463 [1990]). Multicellular spheroids were generated with BTL105 cells and incubated either in the presence of an antibody to TAX-1, or with isotype specific rabbit immunoglobulins as a control. The migration of adherent single cells away from the spheroid was monitored at different time points. In control cultures, migration of single cells was observed after fifteen hours in culture, and by 40 hours, a substantial migration was noted, as shown in FIG. 5. FIG. 5*a* shows three representative BTL105 spheroids 40 hours after plating that were untreated ("Cntl") or treated with the indicated antibody. Migration distances were obtained by measuring the distance between the peripheral edge of the spheroid and the outermost edge of the ring of migrated cells. Each data point in the graphs seen in FIG. 5b and FIG. 5c is an average of three separate experiments showing the standard deviations (indicated by error bars). A summary of the migration distances measured for antibody-treated spheroids is provided in FIG. 5b where a summary of the cell migration measurements in the presence of 1 µM AS1 or Scr1 or untreated over time is provided in FIG. 5c.

It was also determined that downregulation of the TAX-1 message inhibits cell migration. U87 or BTL105 spheroids were cultured in the presence of a 24-base antisense oligonucleotide (AS1) 5'-TCCTGGTGGCTGTCCCCATGGTGG-3' (SEQ ID NO:1) spanning the start codon of the TAX-1 cDNA (See, Genbank accession # X68274 for mRNA; FIG. 6; [SEQ ID NO:5]) or in the presence of a scrambled oligonucleotide (Scr1) with an identical base composition (but not primary sequence). Using specific radiolabeled forward and unlabeled reverse primers for the TAX-1 and GAPDH genes, quantitative RT/PCR was performed within the linear range of product amplification. The level of TAX-1 mRNA in treated or untreated cells was determined by the intensity of TAX-1 relative to the product obtained for GAPDH. AS1 was found to profoundly reduce the level of the TAX-1 message compared to the level seen in untreated cells or cells treated with Scr1. FIG. 5d shows RT/PCR products of the TAX-1 and GAPDH RNA from oligonucleotide treated cells. Sixty-five hours after plating, total RNA was extracted from BTL105 cells that were untreated (Cntl) or treated with either 1.0 µM of AS1 or Scr1. BTL105 cells treated with AS1 had markedly reduced migration away from the spheroids as compared to untreated cells or cells treated with Scr1. A similar inhibitory effect of the antisense oligonucleotide was observed with U87 cells. These results demonstrate that blocking TAX-1 protein inhibited cell migration. Both anti-TAX-1 antibody and antisense treatment inhibited cell migration, but had no effect on cell survival, as determined by MTT assays (See, Example 4).

During tumorigenesis, newly formed tumor cells expand and infiltrate into surrounding tissue by changing their intra-extracellular architecture (Pilkington, Brain Pathol., 4:157 [1994]). It has been shown that altering the expression of adhesion molecules alters the capacity for cell-cell or cell-matrix interaction which can thus mediate the invasion and growth of neoplastic tissue (Pignatelli and Vessey, Hum. Pathol., 25:849 [1994]).

Experiments conducted during the development of the present invention demonstrate that the gene for the axonal cell adhesion molecule TAX-1 is amplified and aberrantly expressed in high grade gliomas. TAX-1, like its rat and chick homologues TAG-1 and axonin-I respectively, is exclusively expressed in the neuronal lineage (See e.g., Hasler et aL, supra). Another member of the Ig superfamily, L1, has been shown to be expressed in glioma cells in culture and potentially involved in the invasion of tumor cells, as a secreted form (Izumoto et al., Cancer Res., 56:1440 [1996]). Unlike TAX-1 however, L1 is expressed in normal glial cells as well as other non-neuronal cells, and therefore does not present as precise a marker as TAX-1. The experiments conducted during the development of the present invention demonstrate that the aberrant expression of TAX-1 in neoplastic cells of high grade gliomas is related to the ability to migrate and invade surrounding normal tissue. Methods of the present invention that restrict expression of TAX-1 or alter TAX-1 effects provide an intervention for glioma therapy and for analyzing and characterizing the TAX-1 function and the effect of other factors (e.g., drugs) on TAX-1 expression and function.

I Antisense Applications

The present invention employs compositions comprising oligomeric antisense compounds, particularly oligonucleotides, for use in modulating the function of nucleic acid molecules encoding TAX-1, ultimately modulating the amount of TAX-1 produced. This is accomplished by providing antisense compounds that specifically hybridize with one or more nucleic acids encoding TAX-1. As used herein, the terms "target nucleic acid" and "nucleic acid encoding TAX-1" encompass DNA encoding TAX-1, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of TAX-1. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding TAX-1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding TAX-1, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2. degree ° C. and are presently preferred base substitutions, even more particularly when combined with 2'-O-methoxyethyl sugar modifications. Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the present invention involves chemically linking to the oligonucleotide one or more moieties or conjugates which enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety. Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the present invention also includes prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the present invention, for example, are prepared as SATE [(S-acetyl-2-thioethyl)phosphate] derivatives according to the methods disclosed in WO 93/24510 in WO94/26764.

The term "pharmaceutically acceptable salts" refers to physiologically and pharmaceutically acceptable salts of the compounds of the invention (i.e., salts that retain the desired biological activity of the parent compound and do not impart undesired toxicological effects thereto). Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine. The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations include, but are not limited to, alkaline, alkaline earth, ammonium and quaternary ammonium cations. Carbonates or hydrogen carbonates are also contemplated.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder that are treated by modulating the expression of TAX-1 is treated by administering antisense compounds in accordance with this invention. The compounds of the present invention are utilized in pharmaceutical compositions by adding an effective amount of an antisense compound to a suitable pharmaceutically acceptable diluent or carrier. Use of the antisense compounds and methods of the invention may also be useful prophylactically (e.g., to prevent tumor formation or metastasis).

The antisense compounds of the invention are useful for research and diagnostics, because these compounds hybridize to nucleic acids encoding TAX-1, enabling sandwich and other assays to easily be constructed to exploit this fact. Hybridization of the antisense oligonucleotides of the invention with a nucleic acid encoding TAX-1 can be detected by means known in the art. Such means may include conjugation of an enzyme to the oligonucleotide, radiolabelling of the oligonucleotide or any other suitable detection means. Kits using such detection means for detecting the level of TAX-1 in a sample may also be prepared.

The present invention also includes pharmaceutical compositions and formulations that include the antisense compounds of the present invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams.

Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid (e.g., nucleic acid encoding TAX-1) and one or more additional antisense compounds targeted to a second nucleic acid target (e.g., nucleic acids encoding factors involved in cell migration, proliferation, etc). Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 $\mu$g to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 $\mu$g to 100 g per kg of body weight, once or more daily, to once every 20 years.

II Antibody Applications

The present invention provides isolated antibodies, preferably monoclonal antibodies, that specifically bind to an isolated polypeptide comprised of at least five amino acid residues of TAX-1. An antibody against the TAX-1 protein of the present invention may be any monoclonal or polyclonal antibody, as long as it can recognize the protein. The antibody against TAX-1 can be produced by using the TAX-1 protein of the present invention as the antigen according to a conventional antibody or antiserum preparation process.

For example, for preparation of a monoclonal antibody, TAX-1 protein, as such, or together with a suitable carrier or diluent is administered to an animal (e.g., mammal) under conditions that permit the antibody production. For enhancing the antibody production capability, complete or incomplete Freund's adjuvant may be administered. Normally, the protein is administered once every 2 weeks to 6. weeks, in total, about 2 times to about 10 times. The animals to be used include, but are not limited to, primates, rabbits, dogs, guinea pigs, mice, rats, sheep, goats, etc.

For preparing monoclonal antibody-producing cells, an individual whose antibody titer has been confirmed is selected from an animal immunized with the antigen (e.g., a mouse) and, 2 days to 5 days after the final immunization, its spleen or lymph node is harvested and antibody-producing cells contained therein are fused with myeloma cells to prepare the desired monoclonal antibody producer hybridoma. Measurement of the antibody titer in an antiserum can be carried out, for example, by reacting the labeled protein, as described hereinafter and an antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1 and PEG (preferably PEG 1000–PEG 6000) is added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody against TAX-1. For example, where a supernatant of the hybridoma is added to a solid phase (e.g., microplate) to which TAX-1 antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the TAX-1 protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody against TAX-1 can be carried out according the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against TAX-1 is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer of anti-TAX-1 in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The TAX-1 protein used herein as the immunogen is not limited to any particular type of immunogen. For example, the TAX-1 protein that is encoded by the TAX-1 gene (further including a TAX-1 gene having a nucleotide sequence partly altered) can be used as the immunogen. Further, fragments of the TAX-1 protein may be used. Fragments may be obtained by any methods including, but not limited to expressing a fragment of the TAX-1 gene, enzymatic processing of the TAX-1 protein, chemical synthesis, and the like.

It has been shown that the fibronectin domains of TAX-1, as a group, are necessary and sufficient for TAX-1's homophilic binding as indicated by the ability of cells expressing different domains of TAX-1 to aggregate (Tsiortra et al., J. Biol. Chem., 271:29216 [1996]). Thus, in certain embodiments of the present invention, antibodies are generated to the fibronectin domains of TAX-1. Another study has examined the expression of L1, a cell adhesion molecule with a similar structure to TAX-1, in gliomas (Izumoto et al., Cancer Research 56:1440 [1996]). It was shown that polyclonal antibodies to the IgG-like domain of L1 inhibited the migration of the tumor cells. Thus, in certain embodiments of the present invention, antibodies are generated to the IgG domain of TAX-1. However, in preferred embodiments, a group of monoclonal antibodies to different region of the IgG domain and/or other domains of TAX-1 are used (i.e., "polymonoclonal antibody therapy") to increase the effectiveness of targeting glioma cells that show antigenic heterogeneity. The selection of suitable antibodies with the desired effect can be identified using cell migration assays as described herein (See e.g., Bjerkvig et al., J. Neurosurg., 72:463 [1990]).

III Genetic Applications

The present invention contemplates the use of any genetic manipulation for use in modulating TAX-1 expression. Examples of genetic manipulation include, but are not limited to, gene knockout (e.g., removing the TAX-1 gene from the chromosome using, for example, recombination), expression of antisense constructs with or without inducible promoters, and the like. Delivery of nucleic acid construct to cell in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. patent application Ser. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administrations is via the blood or lymphatic circulation (See e.g., PCT publication 99/02685 herein incorporated by reference in its entirety). Exemplary dose levels of adenoviral vector are preferably 108 to 1011 vector particles added to the perfusate.

IV Cancer Markers

As described herein, the expression of TAX-1 provides a marker for cancers of the central nervous system. Detection of TAX-1 gene expression and/or TAX-1 protein provides means to detect cancers of the central nervous system long before tumor are otherwise detectable using conventional techniques. Thus, any method for detecting the presence of TAX-1 gene expression, mRNA (e.g., hybridization assays such as Northern blots, RNase assays, reverse transcriptase PCR amplification, and the like), and/or protein (e.g., using the antibodies of the present invention) provides an indicator for cancers of the central nervous system and allows for intervention at the early stages of cancer development (e.g., intervention using the methods and compositions of the present invention and/or conventional therapies).

For example, in one embodiment of the present invention TAX-1 expression is detected with an immunoassay using a TAX-1-specific antibody. For example, a sample (e.g., human tissue, fluid, cell extract, etc.) is collected and a protein extract is prepared using conventional methods. Protein extracts may be separated, for example, using Western blotting techniques, and exposed to the anti-TAX-1 antibody or antibodies.

In some embodiments, anti-TAX-1 antibody is bound to a detectable labeling substance to prepare labelled anti-TAX-1 antibody. The detectable labeling substance should be selected so as to provide sufficient detection sensitivity for TAX-1 assaying. Examples of suitable labeling substances include, but are not limited to, various radioisotopes (e.g., $^{125}$I), various enzymes (e.g., β-D-galactosidase, peroxidase, alkaline phosphatase, glucose oxidase, malate dehydrogenase, etc.), fluorescent substances (e.g., fluorescein, methylumbelliferone, etc.), and metal ions (e.g., magnesium ions).

In one embodiment of the present invention, cerebrospinal fluid is collected from a subject by conventional methods and is used as a sample with or without dilution. A predetermined amount of cerebrospinal fluid sample is reacted with a water-insoluble carrier having bound thereon an antibody in a predetermined amount of a buffer. A total amount of the reaction system is preferably from 50 to 1000 μl. It is preferable to use a buffer containing 0.01 to 1% (w/v, based on the total volume of the buffer) of at least one protein, such as albumin or gelatin and having a pH from 4 to 8.5. A preferred reaction temperature is from 2 to 40° C.

The reaction is incubated (e.g., from 10 minutes to 4 days) and labelled anti-TAX-1 antibody is added thereto and further incubated under the conditions described above. After the reaction, the water-insoluble carrier is washed with water or an appropriate buffer, and the labeling substance bound to the water-insoluble carrier is determined. The above-mentioned series of steps are conducted using control samples such as a standard preparation containing a known concentration of TAX-1 and the measured value of the cerebrospinal fluid is compared with the control standard to obtain the level of TAX-1 in the fluid sample. The level of TAX-1 provides an index for detecting cancer (e.g., glioma) or the development of cancer in the subject. In some embodiments of the present invention, the presence of TAX-1 alone, independent of its quantity, provides the appropriate cancer indicator. The above procedure may be used with any desired sample type (e.g., serum or tissue sample such as cancer tissue).

In further embodiments of the present invention, the presence of particular sequences in the genome of a subject are detected. Such sequences include TAX-1 sequences associated with abnormal expression to TAX-1 (e.g., overexpression or expression at a physiological inappropriate time). These sequence include TAX-1 polymorphisms, including polymorphisms in the transcribed TAX-1 sequence (e.g., that effect TAX-1 processing and/or translation) and regulatory sequences such as promoters, enhances, repressors, and the like. These sequences may also include polymorphisms in genes or control sequences associated with factors that affect TAX-1 expression such as transcription factors, and the like. Any suitable method for detecting and/or identifying these sequences is within the scope of the present invention including, but not limited to, nucleic acid sequencing, hybridization assays (e.g., Southern blotting), single nucleotide polymorphism assays (See e.g., U.S. Pat. No. 5,994,069, herein incorporated by reference in its entirety), and the like.

Direct and/or indirect measures of TAX-1 expression may be used as a marker within the scope of the present invention. Because the present invention provides a link between TAX-1 expression and cancer, any indication of TAX-1 expression may be used. For example, the expression, activation, or repression of factors involved in TAX-1 signalling or regulation may be used as surrogate measures of TAX-1 expression, so long as they are reliably correlated with TAX-1 expression, cell migration, and/or cancer.

The present invention also provides kits for detecting the presence of TAX-1 peptides or nucleotides. Kits may include the appropriate detectable moieties such as hybridization probes, amplification enzymes, buffers, and controls (e.g., TAX-1 nucleic acid controls) for nucleic acid detection assays and antibodies, detectable labels, and controls (e.g., TAX-1 protein) for protein detection assays. The kits may also include the appropriate buffers and enzymes for preparing samples (e.g., samples from subjects suspected of having cancer) to isolate or extract the nucleic acid or peptide. The kits may further include instructions for using the above methods.

V Other Applications

The present invention also provides a variety of additional applications. For example, the present invention provides methods and compositions for identifying and characterizing factors involved in TAX-1 regulation, particularly with respect to the role of TAX-1 in cell migration and cancer. Cells are subjected to a particular test condition (e.g., transfected with a gene of interest, exposed to a drug, treated with a compound suspected of regulating TAX-1 expression, etc.) and TAX-1 expression and/or cell migration capability is detected. Such assays may also be conducted in a subject. For example, TAX-1 expression in vivo and/or the presence, growth, or metastasis of cancer is detected in response to a particular test condition. These methods find particular use in identifying agents that inhibit TAX-1 expression in vivo. For example, antisense molecule and the like are tested for their ability to alter TAX-1 expression. In some embodiments of the present invention, cells or subjects to be tested contain a TAX-1 gene linked to a reporter construct to facilitate the detection of TAX-1 expression. In other embodiments of the present invention, cells are transfected with a library of constructs (e.g., an expression library) to identify genes that regulate TAX-1 expression. In yet other embodiments, drug libraries (e.g., drugs suspected of having anti-cancer properties) are screened to identify compound that regulate TAX-1 expression.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); cm (centimeters); mm (millimeters); µm (micrometers); nm (nanometers); ° C. (degrees Centigrade); and Sigma (Sigma Chemical Co., St. Louis, Mo.).

EXAMPLE 1

Preparation of Tissue Samples and Cultured Cells

Twenty-six gliomas were obtained, after informed consent, from patients undergoing tumor resection at the University of Michigan Medical Center and the University of California, San Francisco. Portions of the tumors were fixed in 10% formaldehyde and embedded in paraffin for sectioning while the remainder of the tissue samples were snap frozen in liquid nitrogen and stored at −80° C. for DNA and RNA extraction. In addition, paraffin sections from an additional 17 gliomas were provided by the Department of Pathology, University of Michigan Medical Center. Primary tumor cell cultures were prepared from a GBM by mechanical disaggregation. Viable cells (BTL105) were separated from red blood cells and cellular debris by centrifugation on a layer of Ficoll-Paque (Pharmacia Biotech AB) and maintained in tissue culture flasks in Dulbecco's Modified Eagle Medium (DMEM) supplemented with 10% fetal bovine serum (FBS, Gibco), penicillin (10 units/ml) and streptomycin (0.1 mg/ml).

EXAMPLE 2

Reverse Transcription/PCR

Total RNA was extracted from 19 of the 26 gliomas with TRIzol reagent (Gibco) following the manufacturer's protocol. For each sample, two micrograms of RNA were treated with DNase I (Boehringer Mannheim) at 37° C. for 30 minutes then denatured in the presence of random hexamer primers (Promega). The samples were incubated with Superscript II (Gibco) reverse transcriptase and the resulting cDNA was treated with RNase H (Boehringer Mannheim) and subjected to polymerase chain reaction (PCR) amplification. For screening purposes, forward and reverse primers for TAX-1 (forward: 5'-CACACCTCACCATCCTTCAGTC [SEQ ID NO:2], reverse: 5'-CACATTTATCCTCTGCCCTTCC [SEQ ID NO:3]) and β-actin (Amplimer set #5402-3, Clontech) were added together into the PCR mixture containing Expand High Fidelity enzyme blend (Boehringer Mannheim). Thirty-cycle PCR amplification was carried out using a Perkin Elmer 9600 GeneAmp PCR system thermal cycler. For quantitative RT/PCR of RNA extracted from cells treated with oligonucleotides, cDNA was generated as described above. Forward primers for the human glyceraldehyde 3-phosphate dehydrogenase (GAPDH, Amplimer set #5406-1, Clontech) and TAX-1 genes were end-labeled with γ32P -dATP using T4 polynucleotide kinase (New England Biolabs). The template was amplified for 15 cycles with labeled forward and unlabeled reverse primers for the TAX-1 gene and then adjusted with labeled forward and unlabeled reverse primers for GAPDH and fresh Expand High Fidelity enzyme for an additional 20 cycles of amplification. It was determined that 35 and 20 cycles were within the linear range of amplification for TAX-1 and GAPDH cDNA from treated cells, respectively.

The products were resolved on a 5% urea-polyacrylamide denaturing gel. Vacuum-dried gels were exposed to a phosphorimaging screen (Molecular Dynamics) and analyzed using imaging software (ImageQuant). Background-subtracted values obtained for the level of TAX-1 expression were based on the relative intensity of the TAX-1 PCR product to that obtained for GAPDH.

EXAMPLE 3

Immunostaining

Paraffin section from 29 different gliomas were immunostained with an antibody made against the TAG-1 protein (#3.1C12, at a 1:2 dilution of a hybridoma supernatant). This mouse monoclonal antibody, developed by Thomas M. Jessell and Jane Dodd, was obtained from the Developmental Studies Hybridoma Bank developed under the auspices of the NICHD and maintained by The University of Iowa, Department of Biological Sciences, Iowa City, Iowa 52242. Serial sections were stained with hematoxilin/eosin or with an antibody against GFAP (Dako, at a 1:6400 dilution) using a Ventana ES automated immunostainer and peroxidase-based visualization (Ventana Medical Systems, Tucson, Ariz.).

EXAMPLE 4

Migration Assay

BTL105 or U87 cells were trypsinized from culture dishes and centrifuged at 1200 g for 5 minutes. The cell pellet was resuspended in DMEM supplemented with 10% FBS and plated into 96-well Ultralow-Cluster culture dishes (Costar, #3474) at a density of $4 \times 10^3$ cells/well and incubated under standard culture conditions for 24 hours on a rotating shaker. Under these conditions the cells aggregate and form a single multicellular spheroid. The spheroids were then treated with either a phosphorothiate modified antisense (ASI) oligonucleotide to TAX-1 (5'-TCCTGGTGGCTGTCCCCATGGTGG [SEQ ID NO:1]), a phosphorothiate modified oligonucleotide that is a scrambled version containing the same base composition as AS1 (Scr1, 5'-CCAGCGCCAAGAATGACGCGGACC [SEQ ID NO:4]) at a final concentration of 0.01, 0.1, or 1.0 µM, a rabbit polyclonal antibody against Tax-1 (Transduction Laboratories) or rabbit immunoglobulins (Sigma) at a final concentration of 15 μg/ml. Forty-eight hours after constant agitation, individual spheroids were selected and plated into a well of a 12-well tissue culture dish (Falcon, #3847) in the presence of fresh media replenished with the appropriate oligonucleotide or antibody. Cell migration away from an attached spheroid was monitored at 15, 30, 42, and 65 hours after plating by imaging the tissue culture well with a digital camera (Pixera Visual Communication System, Pixera Corporation). The migration distance, calibrated with a stage micrometer, was measured using the resulting image.

EXAMPLE 5

Restriction Landmark Genome Scanning

The following provides one illustrative example of restriction landmark genome scanning. Genomic DNA is digested with NotI and EcoR V restriction enzymes and the NotI-derived 5' protruding ends are $\alpha$-$^{32}$P-labeled. These fragments are electrophoretically separated in an agarose disc gel, which is subsequently treated with Hinfi to further cleave the fragments in situ. The resulting fragments are separated perpendicularly in a 5.25% polyacrylamide gel (33 cm×46 cm×0.05 cm). Autoradiograms are obtained.

Autoradiograms are digitized with a Kodak charge-coupled device camera, resulting in images of 1024×1024 pixels at a resolution of 0.344 mm per pixel in both dimensions, each pixel having 1 of 256 possible density values. Software to detect and quantify DNA fragments and software for the camera are obtained from BioImage (Ann Arbor, Mich.). Density readings are calibrated against a wedge with steps of known optical density. Spot intensities (i.e., integrated density) are expressed as optical density units×mm$^2$.

The density of any spot that appears on the gel is in the usual case expected to be determined by two homologous DNA fragments. This system will detect genetic variation of two types, namely, (i) that due to gain or loss of a cut site for the three restriction fragment enzymes employed, and (ii) that due to insertion/deletion/rearrangement events. In the presence of a detectable variant in fragment length resulting from either reason above, only on DNA fragment would be at the usual position, and the autoradiographic intensity of this spot should decrease by 50%. With respect to the variant fragment, it will migrate to an altered position on the gel (a new spot), not enter the gel, or migrate off the gel. New spots may also appear on the gel as a result of variation in fragment that does not normally appear on the gel. Some insertion/deletion/rearrangement events could eliminate a second fragment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for detecting high grade glioma in a subject suspected of having high grade glioma comprising detecting the presence of a TAX-1 protein or polypeptide encoded by the nucleic acid of SEQ ID NO:5 in a glioma sample from said subject; thereby detecting high grade glioma in said subject.

2. The method of claim 1, wherein said subject comprises a human subject.

3. The method of claim 1, wherein said detecting the presence of TAX-1 comprises detecting a TAX-1 protein encoded by SEQ ID NO:5.

4. The method of claim 3, wherein said detecting TAX-1 protein comprises exposing said TAX-1 protein to a TAX-1 specific antibody and detecting the presence of said antibody.

5. The method of claim 1, wherein said detecting the presence of TAX-1 comprises comparing the amount of TAX-1 protein encoded by SEQ ID NO:5 in said sample to an amount of TAX-1 protein present in a control sample.

6. A method for detecting high grade glioma in a subject suspected of having high grade glioma comprising exposing a glioma sample from said subject to a TAX-1 specific antibody, wherein the binding of said antibody to a TAX-1 protein encoded by the nucleic acid of SEQ ID NO:5 in said glioma sample is indicative of said subject having high grade glioma.

7. The method of claim 6, wherein said sample comprises a biopsy sample.

8. The method of claim 7, wherein said biopsy sample comprises a brain tissue biopsy.

9. The method of claim 6, wherein said high grade glioma is glioblastoma multiform.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tcctggtggc tgtccccatg gtgg                                24

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
cacacctcac catccttcag tc                                  22

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
cacatttatc ctctgccctt cc                    22

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ccagcgccaa gaatgacgcg gacc                  24

<210> SEQ ID NO 5
<211> LENGTH: 4548
<212> TYPE: DNA
<213> ORGANISM: Artificial Sequence
<220> FEATURE:
<223> OTHER INFORMATION: Synthetic

<400> SEQUENCE: 5

| | | | | | |
|---|---|---|---|---|---|
| agcggcccag | acaggggctg | gcggcccggc | cggccccggc | tcaccgactc | gggcagcatc | 60 |
| cacctgcccc | agccaacacc | cttctctcgc | cccaggtcct | ttctcagcct | ccagctgggc | 120 |
| tgtcccccaag | ctgagctgag | gctcttctcc | tccgatcccc | acctctgccc | ggacatccac | 180 |
| catggggaca | gccaccagga | ggaagccaca | cctgctgctg | gtagctgctg | tggcccttgt | 240 |
| ctcctcttca | gcttggagtt | cagccctggg | atcccaaacc | accttcgggc | ctgtctttga | 300 |
| agaccagccc | ctcagtgtgc | tattcccaga | ggagtccacg | gaggagcagg | tgttgctggc | 360 |
| atgccgcgcc | cggcccagcc | ctccagccac | ctatcggtgg | aagatgaatg | gtaccgagat | 420 |
| gaagctggag | ccaggttccc | gtcaccagct | ggtgggggc | aacctggtca | tcatgaaccc | 480 |
| caccaaggca | caggatgccg | gggtctacca | gtgcctggcc | tccaacccag | tgggcaccgt | 540 |
| tgtcagcagg | gaggccatcc | tccgcttcgg | ctttctgcag | gaattctcca | aggaggagcg | 600 |
| agacccagtg | aaagctcatg | aaggctgggg | ggtgatgttg | ccctgtaacc | cacctgccca | 660 |
| ctacccaggc | ttgtcctacc | gctggctcct | caacgagttc | cccaacttca | tcccgacgga | 720 |
| cgggcgtcac | ttcgtgtccc | agaccacagg | gaacctgtac | attgcccgaa | ccaatgcctc | 780 |
| agacctgggc | aactactcct | gtttggccac | cagccacatg | gacttctcca | ccaagagcgt | 840 |
| cttcagcaag | tttgctcagc | tcaacctggc | tgctgaagat | accggctct | ttgcacccag | 900 |
| catcaaggcc | cggttcccag | cagagaccta | tgcactggtg | gggcagcagg | tcaccctgga | 960 |
| gtgcttcgcc | tttgggaacc | ctgtcccccg | gatcaagtgg | cgcaaagtgg | acggctccct | 1020 |
| gtccccgcag | tggaccacag | ctgagcccac | cctgcagatc | cccagcgtca | gctttgagga | 1080 |
| tgagggcacc | tacgagtgtg | aggcggagaa | ctccaagggc | cgagacaccg | tgcagggccg | 1140 |
| catcatcgtg | caggctcagc | tgagtggct | aaaagtgatc | tcggacacag | aggctgacat | 1200 |
| tggctccaac | ctgcgttggg | gctgtgcagc | cgccggcaag | ccccggccta | cagtgcgctg | 1260 |
| gctgcggaac | ggggagcctc | tggcctccca | gaaccgggtg | gaggtgttgg | ctggggacct | 1320 |
| gcggttctcc | aagctgagcc | tggaagactc | gggcatgtac | cagtgtgtgg | cagagaataa | 1380 |
| gcacggtacc | atctacgcca | gcgccagct | agccgtgcaa | gcactcgccc | ctgacttcag | 1440 |
| gctgaatccc | gtgaggcgtc | tgatccccgc | ggcccgcggg | ggagagatcc | ttatcccctg | 1500 |
| ccagccccgg | gcagctccaa | aggccgtggt | gctctggagc | aaaggcacgg | agattttggt | 1560 |
| caacagcagc | agagtgactg | taactccaga | tggcaccttg | atcataagaa | acatcagccg | 1620 |

```
gtcagatgaa ggcaaataca cctgctttgc tgagaacttc atgggcaaag ccaacagcac    1680
tggaatccta tctgtgcgag atgcaaccaa aatcactcta gcccctcaa gtgccgacat     1740
caacttgggt gacaacctga ccctacagtg ccatgcctcc cacgacccca ccatggacct    1800
caccttcacc tggaccctgg acgacttccc catcgacttt gataagcctg agggcacta    1860
ccggagaact aatgtgaagg agaccattgg ggatctgacc atcctgaacg cccagctgcg    1920
ccatgggggg aagtacacgt gcatggccca gacggtggtg gacagcgcgt ccaaggaggc    1980
cacagtcctg gtccgaggtc cgccaggtcc ccaggaggtg gtggtggtga gggacattgg    2040
cgacaccacc atccagctca gctggagccg tggcttcgac aaccacagcc ccatcgctaa    2100
gtacaccctg caagctcgca ctccacctgc agggaagtgg aagcaggttc ggaccaatcc    2160
tgcaaacatc gagggcaatg ccgagactgc acaggtgctg ggcctcaccc cctggatgga    2220
ctatgagttc cgggtcatag ccagcaacat tctgggcact ggggagccta gtgggccctc    2280
cagcaaaatc cggaccaggg aagcagcccc ctcggtggca ccctcaggac tcagcggagg    2340
aggtggagcc cccggagagc tcatcgtcaa ctggacgccc atgtcacggg agtaccagaa    2400
cggagacggc ttcggctacc tgctgtcctt ccgcaggcag ggcagcactc actggcagac    2460
cgcccgggtg cctggcgccg atgcccagta cttgtctac agcaacgaga gcgtccggcc    2520
ctacacgccc tttgaggtca agatccgcag ctacaaccgc cgcggggatg ggcccgagag    2580
cctcactgca ctcgtgtact cagctgagga agagcccagg gtggcccta ccaaggtgtg    2640
ggccaaaggg gtctcatcct cagagatgaa cgtgacctgg gaacccgtgc agcaggacat    2700
gaatggtatc ctcctggggt atgagatccg ctactggaaa gctggggaca agaagcagc    2760
tgcggaccga gtgaggacag cagggctgga caccagtgcc cgagtcagtg gcctgcatcc    2820
caacaccaag taccatgtga ccgtgagggc ctacaaccgg ctggcactg ggcctgccag    2880
cccttctgcc aacgccacga ccatgaagcc ccctccgcgg cgacctcctg gcaacatctc    2940
ctggactttc tcaagctcta gtcttagcat taagtgggac cctgtggtcc ctttccgaaa    3000
tgagtctgca gtcaccggct ataagatgct gtaccagaat gacttacacc tgactcccac    3060
gctccacctc accggcaaga actggataga aatcccagtg cctgaagaca ttggccatgc    3120
cctggtacaa attcggacca cagggcccgg agggggatggg atccctgcag aagtccacat    3180
cgtgaggaat ggaggcacaa gcatgatggt ggagaacatg gcagtccgcc cagcaccaca    3240
ccctggcacc gtcattcc actccgtggc gatgctgatc ctcataggct ccctggagct    3300
ctgatcctgg aacccctccc tctgcgccgc agctggacgc cacctccgac ggacacagcc    3360
agccccttcc tgctgccaag gtggcctgac actgtgccag agagtggctg gttttaaata    3420
cctactttaa acagtgccct ttttgtagga ggtaggatat tttatattct gccgcaggat    3480
agaacccacg caaggatttt ctttaaattg agaggcacca gcagtaact tccatgatga    3540
cactgacgcc tatcctgag ctctaggctg cctggaggga aggaacaggc ccatgggaag    3600
aaggggtttt aaaaacatg tcttcaactc agcagagatg ccctctggg accctatacg    3660
cactccgcca cttgagagca gtcctaggcc cggcaggaac accagacatg aacaggttga    3720
agaactggag cgaagtgcac acctcaccat ccttcagtct aaggaagaag ggcaagccct    3780
gggaccaaga gctctcccgc cttctccctc gagcagcagc aaggaccctg acgctgtccc    3840
cgataactcc ctagggctc ctgcctgcc aagcggctga gaaccagcgc ccgatgcct    3900
gaggctggga gcctgagccc cttcagcttt gagggggtg atactccagg ctgtttgggg    3960
tgggagccaa aaagagttga gaggccaggg cccttggtgg aaagggggcac cagccttggt    4020
```

-continued

```
ctgagatagt cacaacccag gtgacgatgc cctctcagcc aacactgcca acctgaccct    4080
gtcatcccga ttgacagcgc cacttcaggt ggctgggtga ctaaagggct tgtcttggtg    4140
gggtctccca cccctccaag acccattctg cacagtccct ccagggtttg ggcaggagat    4200
ggccaatcat gcgcccacct ctccagtgct gcctgcagtc agctcggcct ccccgacctg    4260
cagccccaga ctctgctctc ccagcactga ctcactcctg cctgggaggg gaatgcagca    4320
ttcatgctgg tgtgtcctgg tattgggagg tttctgggaa gggcagagga taaatgtggc    4380
cctgcctgct cccaggtata cctaggacca cctggccaga tccgctccca gacggccttg    4440
gactgcttgc atttccccgg agaaaagggg gttaataaat gggccatcct ttcctgaaaa    4500
aaaaaacccc ccccccccaa aaaaaaaaaa aaaaaaaaaa aaaaaaaa               4548
```